United States Patent
Hu et al.

(10) Patent No.: US 11,537,797 B2
(45) Date of Patent: Dec. 27, 2022

(54) HIERARCHICAL ENTITY RECOGNITION AND SEMANTIC MODELING FRAMEWORK FOR INFORMATION EXTRACTION

(71) Applicant: KONINKLIJKE PHILIPS N.V., Eindhoven (NL)

(72) Inventors: Yiyi Hu, Shanghai (CN); En Ouyang, Shanghai (CN); Zuofeng Li, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 203 days.

(21) Appl. No.: 16/762,684

(22) PCT Filed: Dec. 24, 2018

(86) PCT No.: PCT/EP2018/086863
§ 371 (c)(1),
(2) Date: May 8, 2020

(87) PCT Pub. No.: WO2019/129775
PCT Pub. Date: Jul. 4, 2019

(65) Prior Publication Data
US 2021/0174025 A1    Jun. 10, 2021

(30) Foreign Application Priority Data
Dec. 25, 2017   (WO) ................ PCT/CN2017/118217

(51) Int. Cl.
*G06F 40/295*    (2020.01)
*G06N 20/00*    (2019.01)
(Continued)

(52) U.S. Cl.
CPC .......... *G06F 40/295* (2020.01); *G06F 40/154* (2020.01); *G06F 40/205* (2020.01); *G06F 40/211* (2020.01); *G06F 40/242* (2020.01); *G06F 40/284* (2020.01); *G06F 40/289* (2020.01); *G06F 40/30* (2020.01); *G06N 20/00* (2019.01)

(58) Field of Classification Search
CPC ...... G06F 40/30; G06F 40/211; G06F 40/205; G06F 40/279; G06F 40/295; G06F 40/289; G06F 40/284
See application file for complete search history.

(56) References Cited

U.S. PATENT DOCUMENTS

6,112,168 A  *  8/2000  Corston ................ G06F 40/253
                                                      704/9
6,601,055 B1     7/2003  Roberts
(Continued)

*Primary Examiner* — Samuel G Neway (57) ABSTRACT

Extracting entities from a document with a hierarchical entity graph of entities. Entity definitions and entity recognition definitions are customized by a user and provided. The configuration information is utilized to generate (905) an entity graph, which is then utilized to parse one or more documents. In some implementations, the resulting parse tree may be utilized, in conjunction with user feedback, to generate one or more training instances for a machine learning model assigned to one or more of the custom nodes as an entity recognition definition. Parsing of the resulting tree may be performed with a lazy parsing methodology, with only the portions of interest to the user being identified in the document.

20 Claims, 10 Drawing Sheets

(51) Int. Cl.
    *G06F 40/284*     (2020.01)
    *G06F 40/205*     (2020.01)
    *G06F 40/242*     (2020.01)
    *G06F 40/154*     (2020.01)
    *G06F 40/30*     (2020.01)
    *G06F 40/211*     (2020.01)
    *G06F 40/289*     (2020.01)

(56) References Cited

U.S. PATENT DOCUMENTS

| | | | |
|---|---|---|---|
| 9,536,522 B1 | 1/2017 | Das et al. | |
| 2004/0123277 A1* | 6/2004 | Schrader | G06F 40/221 717/143 |
| 2005/0049852 A1 | 3/2005 | Chao | |
| 2007/0006179 A1* | 1/2007 | Tjong | G06F 8/51 717/136 |
| 2008/0097968 A1 | 4/2008 | Delgado et al. | |
| 2008/0201697 A1* | 8/2008 | Matsa | G06F 40/205 715/237 |
| 2011/0035210 A1 | 2/2011 | Feldman et al. | |
| 2011/0295790 A1 | 12/2011 | Zillner | |
| 2014/0082003 A1 | 3/2014 | Feldman et al. | |
| 2014/0249804 A1* | 9/2014 | Jackson | G06F 40/253 704/9 |
| 2014/0279864 A1* | 9/2014 | Lopyrev | G06F 16/258 707/755 |
| 2016/0180215 A1* | 6/2016 | Vinyals | G06F 40/205 706/20 |
| 2016/0188570 A1* | 6/2016 | Lobez Comeras | G06F 40/211 704/9 |
| 2016/0224543 A1 | 8/2016 | Moitra et al. | |
| 2016/0275073 A1 | 9/2016 | Parikh et al. | |
| 2018/0018676 A1* | 1/2018 | Mukherjee | G06Q 10/10 |
| 2018/0089382 A1* | 3/2018 | Allen | G06F 40/295 |
| 2018/0189269 A1* | 7/2018 | Quirk | G06F 40/295 |
| 2018/0225284 A1* | 8/2018 | Tsukahara | G06F 16/374 |
| 2021/0174025 A1* | 6/2021 | Hu | G06F 40/242 |

* cited by examiner

HIERARCHICAL ENTITY RECOGNITION AND SEMANTIC MODELING FRAMEWORK FOR INFORMATION EXTRACTION

CROSS-REFERENCE TO PRIOR APPLICATIONS

This application is the U.S. National Phase application under 35 U.S.C. § 371 of International Application No. PCT/EP2018/086863, filed on Dec. 24, 2018, which claims the benefit of Patent Application No. PCT/CN2017/118217, filed on Dec. 25, 2017. These applications are hereby incorporated by reference herein.

BACKGROUND OF THE INVENTION

Information extraction, particularly in clinical documents, often requires acquiring key-value pairs that are of interest to clinicians. To complete this task, entity recognition is employed to identify keys and secondly, relationships may be extracted from the identified entities in order to identify meaningful entities in the documents. In traditional methods to extract meaningful related entities, two methodologies are commonly employed: named entity extraction (i.e., NER) and entity relationship extraction (i.e., ER). Existing methodologies require a set of handcrafted (e.g., user-curated) rules or heuristics, often in the form of regular expressions, to identify entities in a document. Regular expressions are useful in many aspects because they are fast to create and need little data for running and testing samples, and further because they are concise in generation and presentation. However, regular expressions when used for identifying entities are still limited in their simplicity. Machine learning methodologies, on the other hand, are more robust, but suffer from difficulties in determining whether the trained machine models are indeed extracting "true" data and require verification to verify whether a given model is properly identifying entities in a document.

Further, in a clinical document, some information may be difficult to extract utilizing rules-based or machine learning based methodologies alone. For example, a document may include information regarding a number of tumors for a patient, but may not include a specified number of tumors. Semantic extraction may prove difficult utilizing a rules or machine learning approaches alone because, semantically, each tumor may be semantically described differently and any particular rule or trained machine learning model may not be capable alone of identifying semantic variations.

Thus, a number of deficiencies in previous methodologies has been identified. Specifically, current entity extraction tools are not capable of being handcrafted by a user to fit a particular type of document yet still capable of utilizing machine learning methods. Further, current methodologies make it difficult to incorporate a clinician's knowledge into an extraction task, and clinician expertise and understanding techniques are not properly applied to machine learning schemas. If clinician understanding and expertise were properly applied to or applied in conjunction with machine learning models, performance may be boosted, resulting in better results and better performance.

SUMMARY OF THE INVENTION

This specification is directed generally to methods for parsing a document of a user utilizing entities and entity recognition definitions provided by the user. The user may define a hierarchy of entities, each with a methodology for identifying the entity in a document. The entity definitions are compiled and an entity graph is generated for the definitions. The user may subsequently invoke a parser to identify information from a document, which is generated at runtime from the entity graph and the identified document. Requested entities, and the child entities of the requested entities, are parsed from the document, thus allowing for substantial runtime reduction by eliminating the requirement of modeling an entire document based on the entity graph, regardless of whether the user has interest in all of the represented entities. Subsequent requests for entities from a document may result in already-identified entities being provided and/or may result in additional modeling of the document based on the entity graph. In some implementations, one or more of the entities (e.g., via their respective graph nodes) may be associated with a machine learning model for identifying the entity. Results from the parse tree may be annotated by the user and further utilized to generate training instances for one or more machine learning models, thus allowing for a feedback loop to improve subsequent invocations of entity recognition definitions.

In some implementations, a method performed by one or more processors is provided and includes receiving a configuration file that includes one or more custom entity definitions, and each custom entity definition includes an entity recognition definition; generating an entity graph based on the custom entity definitions, the entity graph defining relationships between the custom entity definitions; identifying a document of interest; parsing the document of interest utilizing the entity graph to generate a document tree; and providing the document tree to a user. Parsing the document of interest may include: identifying a plurality of tokens in the document of interest; determining, for each of the tokens, a document entity, wherein the document entity matches one of the custom entity definitions; and generating, based on the document entities, the custom entity definitions, the relationships between the custom entity definitions, and the document of interest, a document tree, wherein the document tree includes the document entities and relationships between the document entities.

In some implementations, the method may further include: identifying a parser for the document tree, receiving a parse request from the user, parsing the document tree to identify one or more entities responsive to the parse request, and providing output indicative of the responsive entities to the user. In some of those implementations, only the entities responsive to the parse request may be included in the document tree. In some of those versions, the method may further include the steps of: receiving a second parse request from the user, parsing the document tree to identify one or more additional entities responsive to the second parse request, and providing output indicative of the additional entities, wherein only the one or more entities and the one or more additional entities are included in the parse tree.

In some implementations, the method may include the steps of receiving annotation information associated with the document tree, generating one or more training instances based on the document tree and the annotation information, and updating one or more of the entity recognition definitions based on the training instances. In some implementations, at least one of the entity recognition definitions may be a machine learning model.

In some implementations, parsing the document of interest may include parallel parsing of multiple copies of the document of interest and merging the parsed copies. In some of those implementations, the parallel parsing and merging may be performed in accordance with a map and reduce paradigm. In some of those implementations, conflicts between the parsed copies may be resolved by truncating one or more entities in conflict in at least one of the parsed copies. In some of those implementations, conflicts between the parsed copies may be resolved by extending a parent entity to include all of one or more child entities of the parent entity.

In another aspect, a non-transitory computer-readable medium is provided and includes instructions that, in response to execution of the instructions by one or more processors, cause the one or more processors to perform the following operations: receiving a configuration file, wherein the configuration file includes one or more custom entity definitions, and wherein each custom entity definition includes an entity recognition definition; generating an entity graph based on the custom entity definitions, wherein the entity graph defines relationships between the custom entity definitions; identifying a document of interest; parsing the document of interest utilizing the entity graph, wherein parsing the document of interest includes: identifying a plurality of tokens in the document of interest, determining, for each of the tokens, a document entity, wherein the document entity matches one of the custom entity definitions, and generating, based on the document entities, the custom entity definitions, the relationships between the custom entity definitions, and the document of interest, a document tree, wherein the document tree includes the document entities and relationships between the document entities; and providing the document tree to a user.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

DETAILED DESCRIPTION OF EMBODIMENTS

Extracting meaningful entities from a document, particularly when the entities are distributed in a nested manner within the document, often may prove to be a difficult task to perform automatically. In some instances, a rules-based system may be employed, which is easily provided but often is overly strict in the entities that may be extracted by any particular rule. For example, although a user may identify a series of rules for extracting entities in a particular field, the user will often not have a contingent rule for every possible variation of terms that may describe an entity. Thus, rule-based approaches often do not scale. Machine learning methods may be employed as an alternative approach to extract entities. However, machine learning methods require "ground truths;" i.e., known correct answers that may be used to train and later verify the performance of a machine learning model.

Both rules-based systems and machine learning model extraction systems suffer from weaknesses, when employed alone, in gaining semantic level awareness beyond extracting entities and some relations between entities. First, with machine learning methods, a large amount of annotation is required by a curator to identify entities and to verify that machine learning techniques have properly identified entities. Second, and particularly in non-English documents, grammars are not entirely common and/or have variations among different writers. Consequently, rules are not always the same for all authors of a particular type of document. Finally, existing methods have difficulties extracting entities that are present in a nested fashion, such as when an entity is comprised of sub-entities and the parent entity is identifiable by its constituent sub-components (which themselves may be sub-components of additional entities). Accordingly, techniques are described herein to address these deficiencies.

Figure 1:
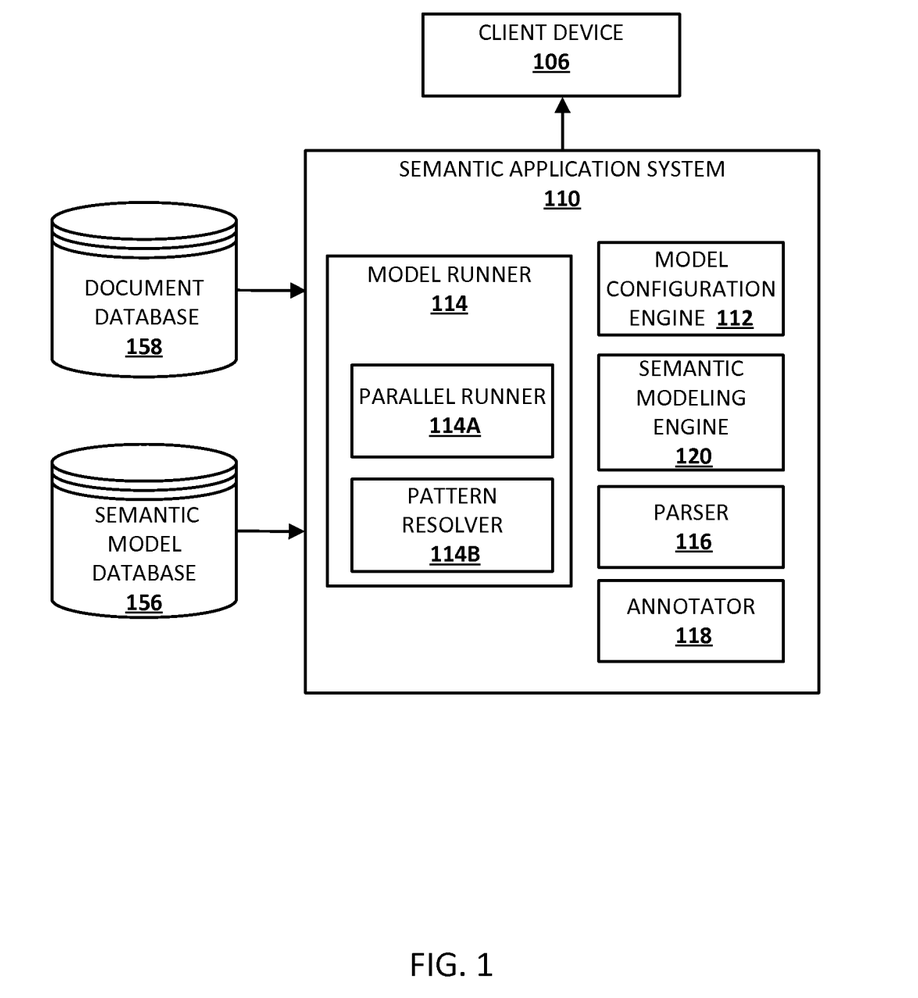
FIG. 1 is a block diagram of an example environment in which embodiments disclosed herein may be implemented.

Now turning to FIG. 1, an example environment in which techniques disclosed herein may be implemented is illustrated. The example environment includes a client device 106 and a semantic application system 110. The client device 106 may be, for example, a standalone voice-activated speaker device, a desktop computing device, a laptop computing device, a tablet computing device, a mobile phone computing device, a computing device of a vehicle of the user, and/or a wearable apparatus of the user that includes a computing device (e.g., a watch of the user having a computing device, glasses of the user having a computing device, a virtual or augmented reality computing device). Additional and/or alternative client devices may be provided.

Although semantic application system 110 is illustrated in FIG. 1 as separate from the client device 106, in some implementations all or aspects of the semantic application system 110 may be implemented by the client device 106. For example, in some implementations, one or more of the components of the semantic application system 110 may be implemented by the client device 106. In implementations where one or more (e.g., all) aspects of the semantic application system 110 are implemented by one or more computing devices remote from the client device 106, the client device 106 and those aspects of the semantic application system 110 communicate via one or more networks, such as a wide area network (WAN) (e.g., the Internet).

Although only one client device 106 is illustrated in combination with the semantic application system 110, in many implementations the semantic application system 110 may be remote and may interface with each of a plurality of client devices of multiple users. For example, the semantic application system 110 may manage communications with each of the multiple devices via different sessions and may manage multiple sessions in parallel. For instance, the semantic application system 110 in some embodiments may be implemented as a cloud-based service employing a cloud infrastructure, e.g., using a server farm or cluster of high performance computers running software suitable for handling high volumes of requests from multiple users. For the sake of simplicity, many examples herein are described with respect to a single client device 106.

The semantic application system 110 includes a model configuration engine 112, a semantic modeling engine 120, a model runner 114, a parser, 116, and an annotator 118. In some implementations, one or more of the components of semantic application system 110 may be omitted, combined, and/or implemented in a component that is separate from the semantic application system 110. Moreover, semantic application system 110 may include additional engines not illustrated herein for the sake of simplicity.

The semantic application system 110 receives instances of user input from the client device 106. User input may include, for example, one or more instances of user-generated entity modeling information (e.g., a user configuration file), and/or user input may include one or more documents to be parsed by a compiled semantic modeler. In some implementations, user input may further include annotations associated with one or more provided documents. In some implementations, one or more documents may be obtained from a database of documents, such as the document database 158. For example, document database 158 may include clinical documents prepared by clinicians after examining patients, e.g., to record aspect(s) of the patients' clinical states, such as number of tumors detected, types of tumors, sizes of tumors, etc.

Generally, the semantic application system 110 provides an interface to allow a user to submit one or more documents and execute a compiled semantic model, based on previous configuration information provided by the user. Model configuration engine 112 receives configuration information from client device 106 and utilizes the configuration information to generate a hierarchical tree of entity recognition information. During configuration, which may be facilitated by one or more applications executing on client device 106, the user is able to define one or more target entities and further define pattern recognition algorithms and/or schemas for each entity. For example, the user may be provided with a graphical user interface that intuitively allows the user to create, drag, drop, and otherwise manipulate nodes that correspond to entities of interest.

Model configuration engine 112 receives the entity definitions and recognition definitions (e.g., recognition schemas and/or algorithms) and creates a configuration file to standardize the entity definitions. For example, a user may utilize one or more interfaces executing on client device 106 to define entities and/or recognition definitions, and the interface may provide the entities and/or other definitions to model configuration engine 112, which may then standardize the information into a single configuration file. Thus, model configuration engine 112 may receive configuration files, graphical user interface ("GUI") input, and/or other scripts to create a configuration file.

As described herein, entities are semantic units that are identifiable in one or more documents. An entity is a meaningful text token, or series of tokens, that are associated with a semantic meaning. In some implementations, an entity may be recognized based on contextual placement within a string of text. For example, an entity of <tumor> may be identified based on one or more contextual markers in a string, such as placement of a <size> entity, a <type> entity, and/or other indicator that one or more tokens in a string are defining and/or referencing a <tumor>.

Semantic modeling engine 120 receives a configuration file from the model configuration engine 112 and generates a compiled entity graph based on the configuration file. A compiled entity graph is based on the custom entity definitions specified by the user, either via a configuration file, a GUI, and/or other provided scripts. The compiled entity graph defines relationships between the custom entity definitions and may be utilized to parse a document of interest. To construct a graph, the semantic modeling engine 120 traverses each entity node in the compiled tree, from the bottom up, and creates graph entities and links for each entity. Further, for each entity, semantic modeling engine 120 associates the specified entity recognition definition with each entity, as specified in the configuration file generated and/or provided to model configuration engine 112.

In some implementations, to create an entity node, an entity template is generated by sematic application 110 and provided to the user via client device 106. The user may then provide the template implementation details, such as entity name and/or specify a particular entity recognition definition for a particular entity. For example, semantic model database 156 may include a plurality of entity recognition definitions that have been previously defined by a user and/or may include a standardized library of recognition definitions. These may include, for instance, regular expressions, conditional random fields ("CRF"), recurrent neural networks ("RNNs"), e.g., long-short term memory ("LSTM") and the combinatory LSTM-CRF The user may specify a particular recognition definition from semantic model database 156 to utilize in identifying an entity, provide an indication of the definition via the provided template, and further provide additional information that may be utilized to recognize the entity in one or more documents. The template, with the user information included, may then be processed by the model configuration engine 112 and/or semantic modeling engine 120 to generate an entity graph. The generated graph may then be stored in semantic model database 156 and/or one or more additional or alternative databases.

Figure 2:
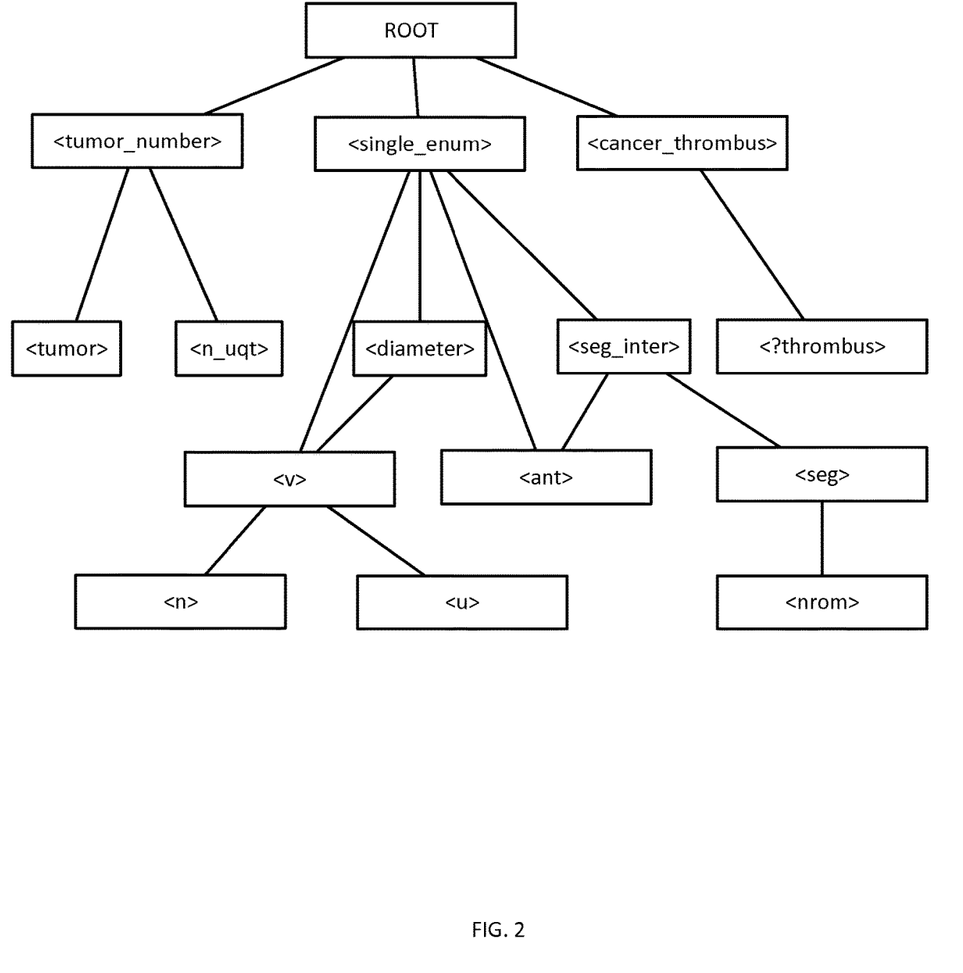
FIG. 2 is an illustration of an example entity graph of entities and relationships between the entities in a hierarchy.

As a working example, a clinical document may include the following text: "Two tumors, one occupied at the right side of the gallbladder inside abdominal cavity sized 1.5× 1.5×1.5 cm" and "Another tumor occupied between VII segment of liver and right side kidney sized 2×2×2 cm, no thrombus at portal vein." In order to identify and extract meaningful information automatically from the given strings, it is necessary for a clinician to first generate a configuration file that includes a hierarchical structure for a <tumor>. Referring to FIG. 2, an example model for a <tumor> entity is provided. The model illustrated in FIG. 2 may be defined by a user via one or more mapping (e.g., GUI) applications executing on client device 106, may be defined in one or more files, and/or may be generated utilizing one or more alternate methods.

As illustrated, the root node is a parent node of all other nodes, which include a <tumor_number> node, a <single_enum> node, and a <cancer_thrombus> node as children. On the second level of the tree, a <tumor> node and <N_UQT> node are provided as children of <tumor_number> node, <diameter> node, and <seg_inter> node as children of <single_enum> node, and <?thrombus> of the <cancer_thrombus> node. A third and fourth level of the tree are provided in the same manner.

As illustrated, entities with masks <N>, <U>, and <N_UQT> define entities for numbers, units, and quantities respectively. The <ant> tag is utilized to define an entity for an anatomical position in general, with the <seg> entity to define a liver segment. Further, a <tumor> entity defines a tumor, and the <?thrombus> entity defines whether thrombus is present (hence the question mark, indicating that the entity may not be present or may be present as a negation). After these basic entities are defined, larger entities comprised of the sub-entities may be defined as combinations of those entities. The <v> entity, for example, is a volume entity and is defined as a <n>, i.e., number. Similarly, a <diameter> entity is defined as a number <n> and unit <u>. Additional defined entities include a <seg_inter> entity to define where a tumor is described as between segments, a <single_enum> entity to describe a single tumor, and a <cancer_thrombus> entity to describe a whole description of a cancer thrombus.

For each of the entities described in FIG. 2, an engine and/or recognition description may be assigned and utilized to identify the given entity in a document. For example, and referring to FIG. 3, a portion of an example configuration file is provided and includes definitions for some of the entities in FIG. 2. The configuration file may be generated by semantic modeling engine 120 and/or may be provided by a user via client device 106. For example, the graph illustrated in FIG. 2 may be generated by a user via one or more applications executing on client device 106 and/or by one or more templates provided to the user by semantic modeling engine 120, and semantic modeling engine 120 may generate the configuration file of FIG. 3 in response to being provided the custom entity definitions and custom entity recognition definitions.

Figure 3:
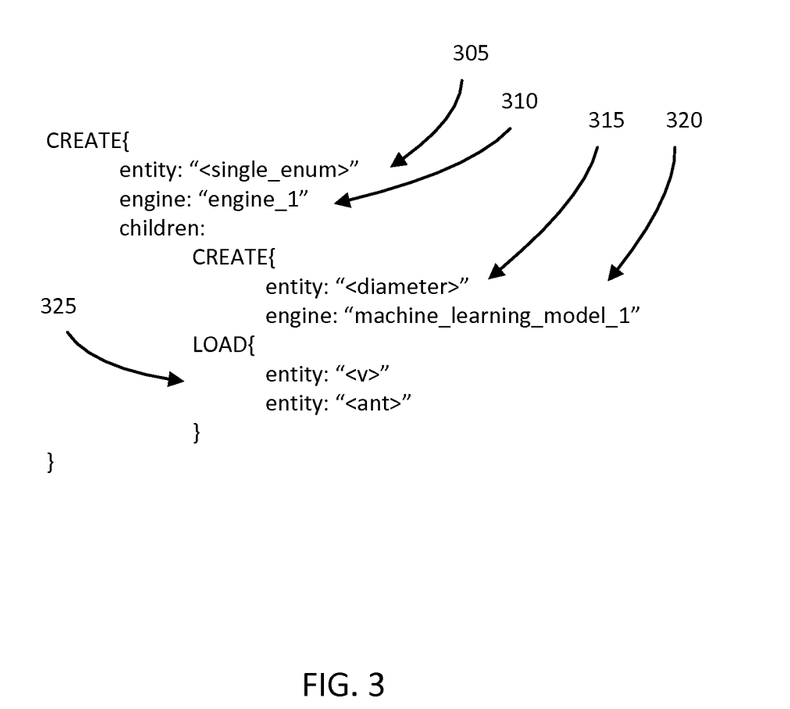
FIG. 3 is a sample configuration file of entities and custom entity recognition definitions.

The configuration file of FIG. 3 includes a definition for a <single_enum> node 305, with a further definition of a custom entity recognition definition 310. Further, the <single_enum> node custom entity definition 305 includes a definition for a child entity, <diameter> 315. The <diameter> entity definition 315 additionally includes a custom entity recognition definition 320. The custom entity recognition definitions that are referenced in FIG. 3 may be custom recognition models, such as machine learning models (e.g., CNNs, LSTM, etc.), stored in one or more databases, such as semantic model database 156. In some implementations, the custom entity recognition definitions may be personal to the user and/or may be publicly available models and/or definitions. Other examples of entity recognition definitions were mentioned previously, and may include, for example, regular expressions, conditional random fields, recurrent neural networks, such as long-short term memory and combinatory long-short term memory networks, and/or other methods for entity recognition schemas.

For example, conditional random fields (CRFs) are a class of sequence modeling methods which, unlike discrete classifiers, take context into account during sequence labeling task. CRFs commonly are used for applications such as part of speech tagging, shallow parsing and named entity recognition (NER). Annotated textual sequence with labels as well as specially designed feature templates are required in order to train CRFs for specific sequence labeling task. Therefore, task specific knowledge must be developed to create linguistic feature template for training. Feed-forward neural networks with fixed window size, and recurrent neural networks may be used for sequence label classification and achieved great success. Long-short-term Memory networks, or "LSTMs", are designed to avoid the long dependency problems, where remembering information for a long period of time is a default behavior. As a result, they are suitable for learning long dependency contextual features in a sequence.

In some implementations, one or more entities may be generated based solely on the information provided in the configuration file. For example, for the <single_enum> entity, a definition is provided. In some implementations, one or more entities may already be defined, either elsewhere in the configuration file or in a different configuration file. For example, the <single_enum> entity definition includes children of <v> and <ant> as a "LOAD" children in the definition, indicating that those entities are defined elsewhere and the already defined definitions, including recognition definitions, need only be loaded into this configuration file. Thus, a user may define an entity once and reuse an entity definition at a later time without having to redefine the entity and its recognition definition. For example, one or more databases may include pre-defined entities and the user may merely specify an identifier of an entity to invoke that entity in a later configuration.

As previously described, the configuration file is generated by model configuration engine 112 and an entity graph is compiled by semantic modeling engine 120. In doing so, the semantic modeling engine 120 traverses the nodes of the entity graph and generates a class for each of the entities, either by loading an existing class or by creating a new class for newly customized entities. Each of the entity classes includes a mask, i.e., the terms in FIG. 2, that are utilized by the model runner to replace entity information in a document.

Model runner 114 then receives an input document (e.g., a clinical write-up or report), either from client device 106 or obtains an input document from document database 158, and executes the compiled entity graph to parse entities from the identified document. The result is a document tree representative of the hierarchy of the entities identified in the document. In some embodiments, model runner 114 follows a map-reduce paradigm, with a parallel runner 114a to perform mapping and a pattern resolver 114b to perform reducing. In the mapping step, the parallel runner 114a executes each entity node in the graph at a given level of the entity graph in parallel (i.e., parses copies of the input document for each entity in a level of the graph) and marks identified entities in each copy of the text. Once multiple copies of the input document have been marked, the pattern resolver 114b merges the marked texts into a single representation of the input document, with all entities marked. Further, pattern resolver 114b resolves potential conflicts between the copies of the text, such as when two entities are identified as occurring in the same portion of the text. Once a canonical version of the text, with all entities marked, has been determined for a level of the graph, the marked text is utilized with the next level of entities in the same manner. Model runner 114 continues to parse the text until a root node of the entity graph is reached.

Figure 4:
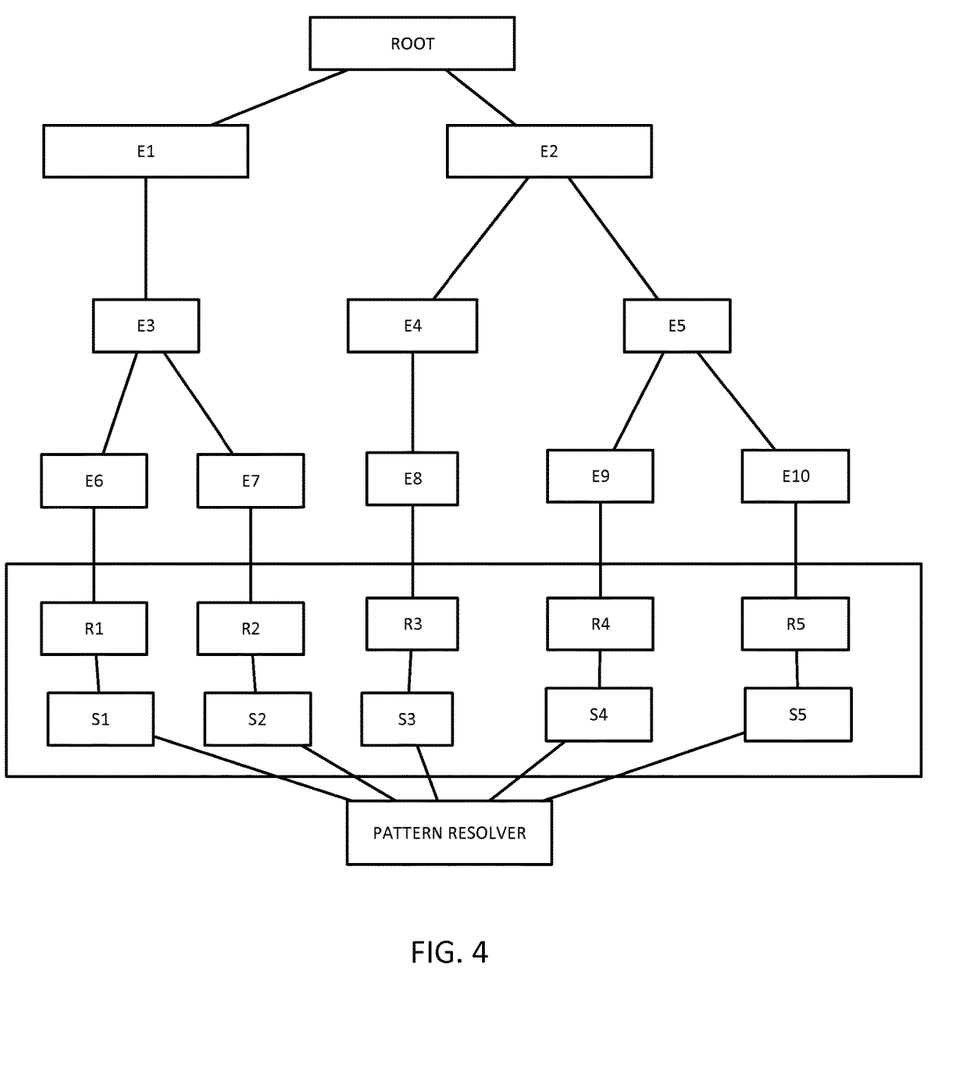
FIG. 4 illustrates a parallel runner and pattern resolver executing a sample text.

Referring to FIG. 4, an illustration of the mapping-reduction of a document is provided. The illustration includes entities that are defined in an entity graph and includes generic entities E1, E2, E3, etc. For each of entities in the bottom level of the graph (i.e., E6-E10), the document is scanned utilizing a copy of the document. Thus, 5 instances of the parallel runner 114a are instantiated (i.e., R1-R5), each of which scans the document for one of the respective entities utilizing the assigned custom entity recognition definition for that entity. The result is five annotated strings (S1-S5), each of which includes annotations for one of the entities. Pattern resolver 114b then combines S1-S5 into a single output space as a pattern tree, with any conflicts resolved by the pattern resolver 114b. When a span of the resulting combined text includes multiple nested entities, pattern resolver 114b adjusts the resulting pattern tree to reflect the hierarchical structure of the entities in the entity graph.

Figure 5:
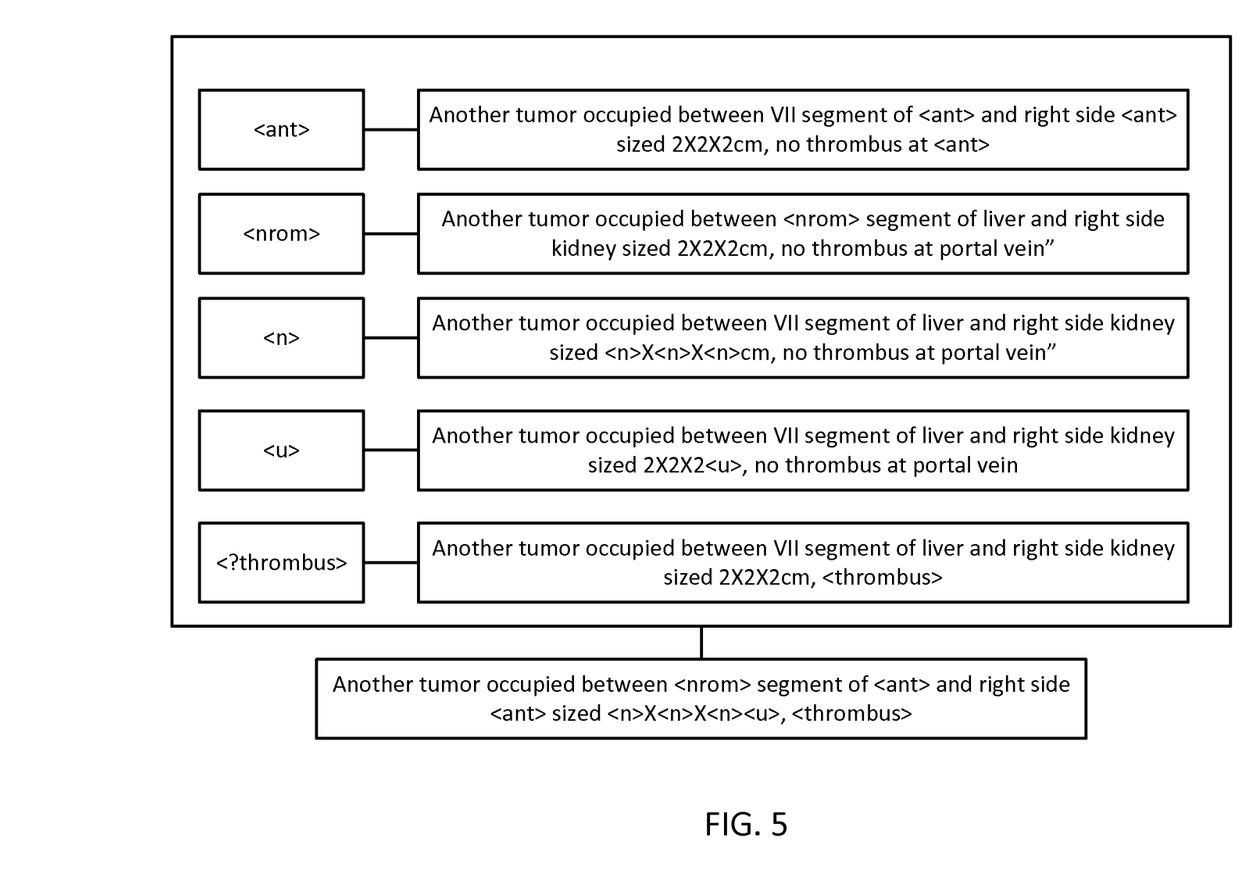
FIG. 5 illustrates a parallel runner resolving multiple instances of annotated text from a pattern resolver.
Figure 6:
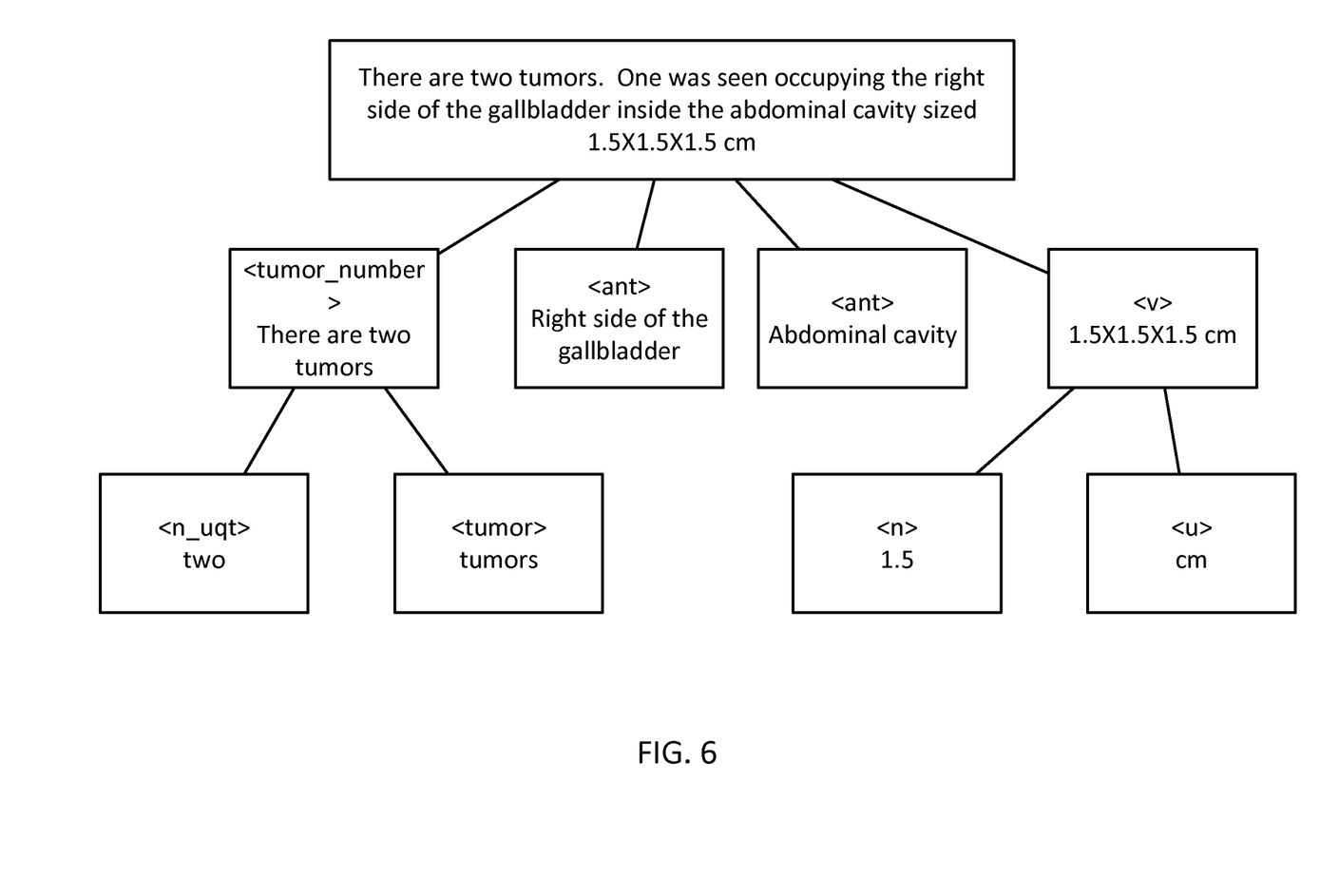
FIG. 6 is an illustration of a text completely annotated based on the entity graph of FIG. 2.

Referring to FIG. 5, an example of the pattern resolver 114b utilizing an example phrase from a document is provided. The phrase "Another tumor occupied between VII segment of liver and right side kidney sized 2×2×2 cm, no thrombus at portal vein" has been identified, and the lowest level of entities have been identified. For example, "2" in the phrase has been identified as an <n> entity (i.e., number), "cm" as a <u> unit entity, "no thrombus at portal vein" as <?thrombus>, "VII" as <nrom>, and "liver," "kidney," and "portal vein" as <ant>. Parallel runner 114a generates each of the identical texts and identifies one of the entities in each of the texts. Pattern resolver 114b combines the individual texts into a single annotated text. Referring to FIG. 6, a completed example text is illustrated and annotated into a pattern tree in the same manner.

In some implementations, conflicting cases may be present when identifying entities. For example, a text string may be identified both as a <diameter> entity and as a <seg_inter> entity, with part of the entities overlapping. In some implementations, a user may define, in the configuration file and/or via an interface when generating a configuration file, a priority level for resolving such conflicts when the entities are on the same level of the entity graph. For example, a user may define <seg_inter> with a priority of "1.0" and <diameter> with a priority of "0.5," indicating that, when the two entities are both identified for a given string or substring, <seg_inter> has priority. The portion that is part of the <diameter> entity that conflicts with the <seg_inter> entity may be truncated from the <diameter> entity in order to resolve the conflict. In some implementations, one or more additional methods may be utilized to resolve such conflicts. For example, a heuristic approach may include identifying which of the entities has been associated with the overlapping information in past documents and assign a score for each of the entities. Then, the entity with the higher score may then be assigned the overlapping text over the lower scoring entity. In some implementations, the first entity assigned to a string may be the final entity and any subsequent entities may be truncated, thus preserving the first entity as the "correct" entity for the string.

Figure 7:
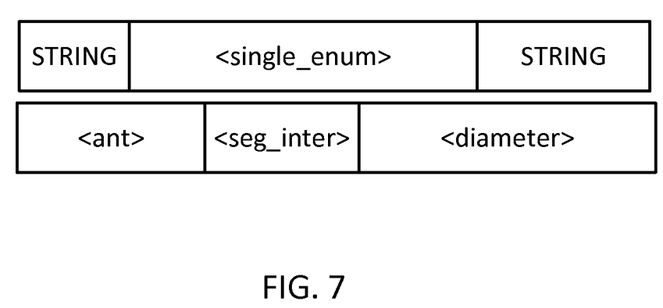
FIG. 7 is an illustration of a conflict between a parent entity and child entities.

In some implementations, conflicts may exist between layers of the entity graph. For example, referring to FIG. 7, illustrations of two different identifications of a string, one with a parent entity and one with three child entities, is provided. For example, an entity may be comprised of an <ant> entity, a <seg_inter> entity, and a <diameter> entity, as illustrated in FIG. 7. The <single_enum> entity has been identified as spanning part of the <ant> entity, all of the <seg_inter> entity, and part of the <diameter> entity in a string. Pattern resolver 114b may readjust the boundaries of <single_enum> to include all of the <ant> entity and all of the <diameter> entity to preserve the hierarchical relationship between the entities and prevent unnecessary truncation of any information in the resulting pattern tree.

Parser 116 allows a user additional functionality in processing the document tree resulting from model runner 114. In some embodiments, parser 116 provides one or more operators (e.g., predefined functions that can be called) to allow the user, via one or more applications executing on client device 106, to iterate, query, and/or other execute the information extracted from the document. For example, once model runner 114 has executed a model and created a document tree for a given document, the document tree may be stored in one or more databases. When the user, via an application executing on client device 106, has interest in utilizing the tagged entities in the document, parser 116 may provide an interface (such as an API) to the client device 106 to allow for meaningful information to be extracted from the document tree.

In some implementations, model runner 114 executes via a laziness design paradigm. Model runner 114 is provided information from a parser regarding only the portions of the entity graph to execute. Thus, only particular portions of the entity graph may be executed, while the remainder of the graph remains a static graph representation, as produced by the model configuration engine 112.

Figure 8:
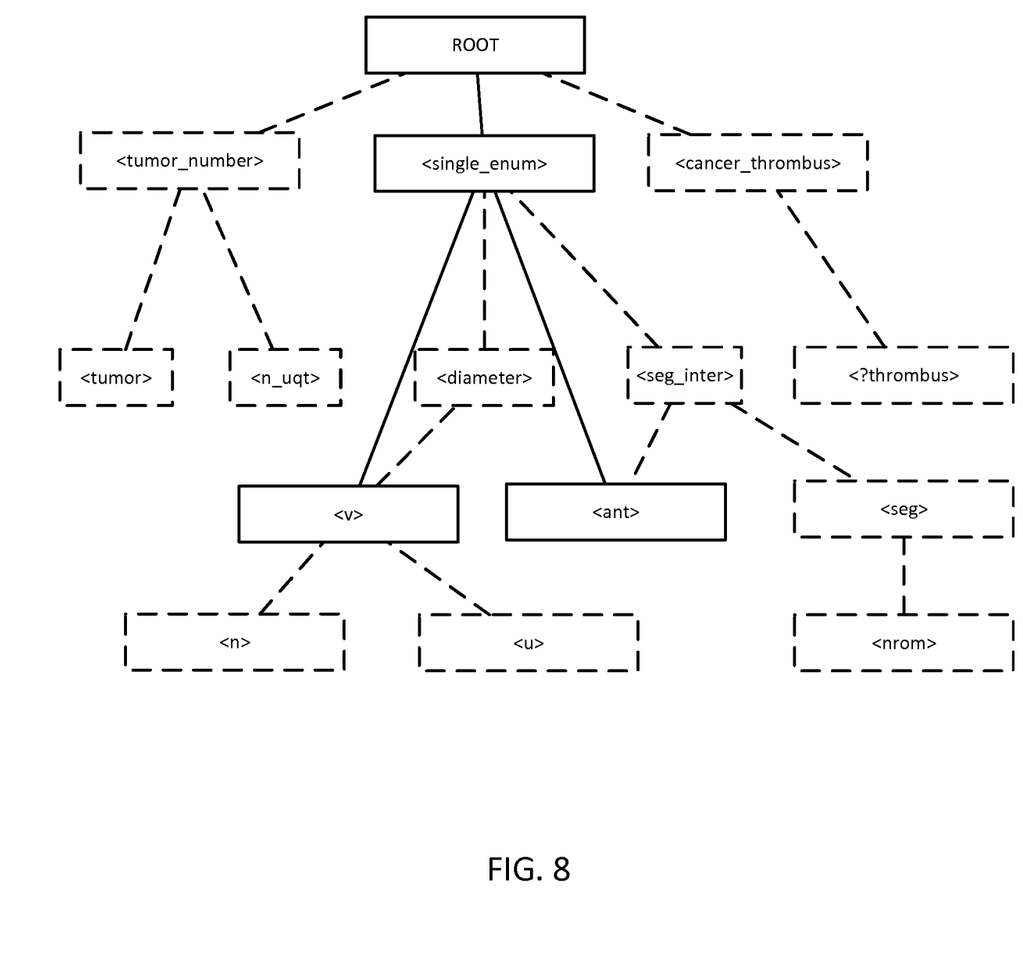
FIG. 8 is an illustration of entities in an entity graph that are resolved at runtime based on a parser command.

For example, referring to FIG. 8, an example of the model runner 114 executing a lazy approach is provided. The parser 116 may provide a command to "Get next <single_enum>," which indicates that an application utilizing the parser 116 has interest in just a <single_enum>. When executing the command, the model runner 114 only accesses the portion of the tree that includes sub-entities of the <single_enum> entity and not other portions of the pattern tree (i.e., the entities and relationships illustrated with dotted lines). Any other nodes of the pattern tree are left unresolved, thus preventing unnecessary computation time in constructing the entire tree at runtime. As additional entities are requested by the parser 116, the model runner 114 may then utilize the parallel runner 114a and pattern resolver 114b to resolve and identify the later-requested entities. The semantic model may be stored in the semantic model database 156 as a partially resolved tree, accessed at a later time when additional entities are requested, and the new tree may then be stored in its place in database 156.

Annotator 118 allows for ground-truth annotations to output from the semantic application system 110. Because one or more of the entity recognition definitions may be a machine learning model (as described herein), annotations provided via the annotator 118 may be utilized to verify that the models underlying the recognition algorithms are identifying entities with acceptable accuracy. For example, a user may curate output from the semantic application system 110 with corrections to entity identification via the annotator 118. The resulting corrections may be utilized to further train one or more of the machine leaning models utilized as an entity recognition definition and/or may be utilized to verify future results from one or more model utilized in entity recognition.

For example, referring again to FIG. 3, the <diameter> entity is created with a custom entity recognition definition of "machine_learning_model_1," which may be a machine learning model that has been trained based on previous training data. Once model runner 114 identifies a <diameter> entity and the parser 116 provides the entity to the user, the user may identify that the <diameter> entity is not correct (or alternatively, confirm that the entity was correctly identified). The user may utilize the annotator 118 to annotate the results and one or more components may update "machine_learning_model_1" to reflect the truth information provided by the user. Thus, the annotated results may be utilized as a training instance for the machine learning model and/or may be utilized in the future to verify that an entity identified as <diameter> is "correct." In some implementations, multiple machine learning models may be updated based on a single annotation. For example, a <diameter> entity may be a child entity of one or more other entities, and the machine learning models associated with the parent entities may also be updated and/or retrained based on the user annotation of results.

Figure 9:
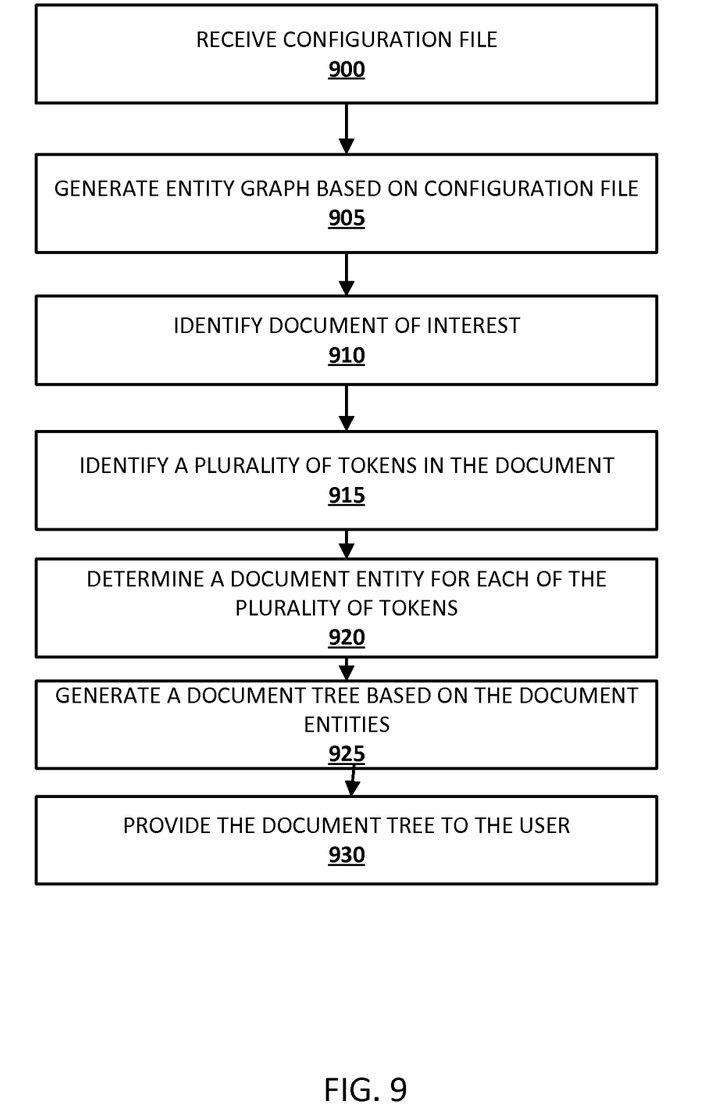
FIG. 9 is a flowchart illustrating an example implementation of methods described herein.

Referring to FIG. 9. A flowchart is provided illustrating an example implementation of methods described herein. In some implementations, additional steps may be included and/or one or more steps may be omitted.

At step 900, a configuration file is received. The configuration file may be provided by a component that shares one or more characteristics with device 106. The configuration file may include one or more custom entity definitions as well as definitions for methods for recognizing entities in a text. For example, the user may utilize one or more tools executing on device 106 to define entities, and assign a recognition algorithm to each of the entities.

At step 905, an entity graph is generated based on the custom entity definitions in the configuration file. The entity graph determines, based on the configuration file, how custom entities are related, such as instances when an entity is comprised of other entities. For example, a "volume" entity may be comprised of three "number" entities and a "unit" entity. Based on the custom entity definitions, an entity graph is generated reflecting the relations between the entities.

At step 910, a document of interest is identified. The document of interest may be provided by device 106 and/or one or more components may identify a document stored in one or more databases. The document of interest may be, for example, a text document and include one or more strings that the user has interest in parsing to identify custom entities, as defined in the configuration file.

At step 915, a plurality of tokens is identified in the document of interest. The tokens may be strings of text of varying length and may be identified based on one or more tokenizing techniques. At step 920, for each of the tokens, a document entity is determined.

The document entities are determined based on the custom entity definitions in the configuration file as well as the custom recognition definitions provided in the configuration file. At step 925, a document tree is generated based on the identified document entities. The document tree includes the tokens identified in the document, each tagged with a custom entity as described in the configuration file.

At step 930, the document tree is provided to the user. The document tree may then be utilized by a parser to extract entities from the document and provide the user with entity information from the document. For example, the user may utilize a parser to extract all "tumor" entities from a document.

Figure 10:
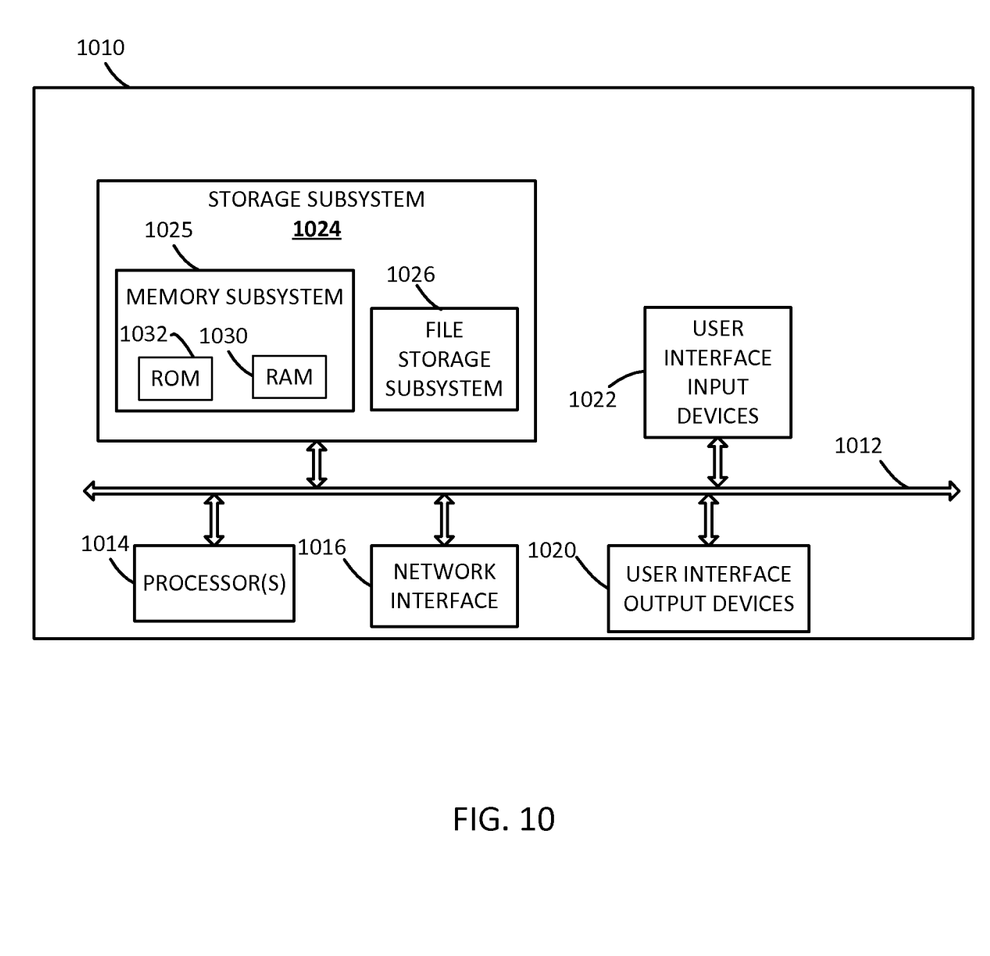
FIG. 10 illustrates an example architecture of a computing system.

FIG. 10 is a block diagram of an example computing device 1010 that may optionally be utilized to perform one or more aspects of techniques described herein. In some implementations, one or more of device 106, semantic application system 110, and/or other component(s) may comprise one or more components of the example computing device 1010.

Computing device 1010 typically includes at least one processor 1014 which communicates with a number of peripheral devices via bus subsystem 1012. These peripheral devices may include a storage subsystem 1024, including, for example, a memory subsystem 1025 and a file storage subsystem 1026, user interface output devices 1020, user interface input devices 1022, and a network interface subsystem 1016. The input and output devices allow user interaction with computing device 1010. Network interface subsystem 1016 provides an interface to outside networks and is coupled to corresponding interface devices in other computing devices.

User interface input devices 1022 may include a keyboard, pointing devices such as a mouse, trackball, touch-pad, or graphics tablet, a scanner, a touchscreen incorporated into the display, audio input devices such as voice recognition systems, microphones, and/or other types of input devices. In general, use of the term "input device" is intended to include all possible types of devices and ways to input information into computing device 1010 or onto a communication network.

User interface output devices 1020 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computing device 1010 to the user or to another machine or computing device.

Storage subsystem 1024 stores programming and data constructs that provide the functionality of some or all of the modules described herein. For example, the storage subsystem 1024 may include the logic to perform selected aspects of the method(s) described herein.

These software modules are generally executed by processor 1014 alone or in combination with other processors. Memory 1025 used in the storage subsystem 1024 can include a number of memories including a main random access memory (RAM) 1030 for storage of instructions and data during program execution and a read only memory (ROM) 1032 in which fixed instructions are stored. A file storage subsystem 1026 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 1026 in the storage subsystem 1024, or in other machines accessible by the processor(s) 1014.

Bus subsystem 1012 provides a mechanism for letting the various components and subsystems of computing device 1010 communicate with each other as intended. Although bus subsystem 1012 is shown schematically as a single bus, alternative implementations of the bus subsystem may use multiple busses.

Computing device 1010 can be of varying types including a workstation, server, computing cluster, blade server, server farm, or any other data processing system or computing device. Due to the ever-changing nature of computers and networks, the description of computing device 1010 depicted in FIG. 10 is intended only as a specific example for purposes of illustrating some implementations. Many other configurations of computing device 1010 are possible having more or fewer components than the computing device depicted in FIG. 10.

The invention claimed is:

1. A method implemented by one or more processors, comprising:
receiving a configuration file, wherein the configuration file includes one or more custom entity definitions, and wherein each custom entity definition includes an entity recognition definition;
generating an entity graph based on the custom entity definitions, wherein the entity graph defines relationships between the custom entity definitions;
identifying a document of interest;
parsing the document of interest utilizing the entity graph, wherein parsing the document of interest includes:

identifying a plurality of tokens in the document of interest, determining, for each of the tokens, a document entity, wherein the document entity matches one of the custom entity definitions, and generating, based on the document entities, the custom entity definitions, the relationships between the custom entity definitions, and the document of interest, a document tree, wherein the document tree includes the document entities and relationships between the document entities; and providing the document tree to a user.

2. The method of claim 1, further comprising;
identifying a parser for the document tree;
receiving a parse request from the user;
parsing the document tree to identify one or more entities responsive to the parse request; and
providing output indicative of the responsive entities to the user.

3. The method of claim 2, wherein only the entities responsive to the parse request are included in the document tree.

4. The method of claim 3, further comprising:
receiving a second parse request from the user;
parsing the document tree to identify one or more additional entities responsive to the second parse request; and
providing output indicative of the additional entities, wherein only the one or more entities and the one or more additional entities are included in the document tree.

5. The method of claim 1, further comprising:
receiving annotation information associated with the document tree;
generating one or more training instances based on the document tree and the annotation information; and
updating one or more of the entity recognition definitions based on the training instances.

6. The method of claim 1, wherein at least one of the entity recognition definitions is a machine learning model.

7. The method of claim 1, wherein parsing the document of interest includes parallel parsing of multiple copies of the document of interest and merging the parsed copies.

8. The method of claim 7, wherein the parallel parsing and merging are performed in accordance with a map and reduce paradigm.

9. The method of claim 7, wherein conflicts between the parsed copies are resolved by truncating one or more entities in conflict in at least one of the parsed copies.

10. The method of claim 7, wherein conflicts between the parsed copies are resolved by extending a parent entity to include all of one or more child entities of the parent entity.

11. At least one non-transitory computer-readable medium comprising instructions that, in response to execution of the instructions by one or more processors, cause the one or more processors to perform the following operations:

receiving a configuration file, wherein the configuration file includes one or more custom entity definitions, and wherein each custom entity definition includes an entity recognition definition;

generating an entity graph based on the custom entity definitions, wherein the entity graph defines relationships between the custom entity definitions;

identifying a document of interest;

parsing the document of interest utilizing the entity graph, wherein parsing the document of interest includes:

identifying a plurality of tokens in the document of interest, determining, for each of the tokens, a document entity, wherein the document entity matches one of the custom entity definitions, and generating, based on the document entities, the custom entity definitions, the relationships between the custom entity definitions, and the document of interest, a document tree, wherein the document tree includes the document entities and relationships between the document entities; and providing the document tree to a user.

12. The non-transitory computer-readable medium of claim 11, further comprising;
identifying a parser for the document tree;
receiving a parse request from the user;
parsing the document tree to identify one or more entities responsive to the parse request; and
providing output indicative of the responsive entities to the user.

13. The non-transitory computer-readable medium of claim 12, wherein only the entities responsive to the parse request are included in the document tree.

14. The non-transitory computer-readable medium of claim 13, further comprising:
receiving a second parse request from the user;
parsing the document tree to identify one or more additional entities responsive to the second parse request; and
providing output indicative of the additional entities, wherein only the one or more entities and the one or more additional entities are included in the document tree.

15. The non-transitory computer-readable medium of claim 11, further comprising:
receiving annotation information associated with the document tree;
generating one or more training instances based on the document tree and the annotation information; and
updating one or more of the entity recognition definitions based on the training instances.

16. The non-transitory computer-readable medium of claim 11, wherein at least one of the entity recognition definitions is a machine learning model.

17. The non-transitory computer-readable medium of claim 11, wherein parsing the document of interest includes parallel parsing of multiple copies of the document of interest and merging the parsed copies.

18. The non-transitory computer-readable medium of claim 17, wherein the parallel parsing and merging are performed in accordance with a map and reduce paradigm.

19. The non-transitory computer-readable medium of claim 17, wherein conflicts between the parsed copies are resolved by truncating one or more entities in conflict in at least one of the parsed copies.

20. A system comprising one or more processors and memory operably coupled with the one or more processors, wherein the memory stores instructions that, in response to execution of the instructions by one or more processors, cause the one or more processors to perform the following operations:

receiving a configuration file, wherein the configuration file includes one or more custom entity definitions, and wherein each custom entity definition includes an entity recognition definition;

generating an entity graph based on the custom entity definitions, wherein the entity graph defines relationships between the custom entity definitions;
identifying a document of interest;
parsing the document of interest utilizing the entity graph, wherein parsing the document of interest includes:
  identifying a plurality of tokens in the document of interest,
  determining, for each of the tokens, a document entity, wherein the document entity matches one of the custom entity definitions, and
  generating, based on the document entities, the custom entity definitions, the relationships between the custom entity definitions, and the document of interest, a document tree, wherein the document tree includes the document entities and relationships between the document entities; and providing the document tree to a user.

* * * * *